(12) United States Patent
Meier et al.

(10) Patent No.: US 8,244,330 B2
(45) Date of Patent: Aug. 14, 2012

(54) INTEGRATED RADIATION THERAPY SYSTEMS AND METHODS FOR TREATING A TARGET IN A PATIENT

(75) Inventors: Eric Meier, Bellevue, WA (US); Timothy P. Mate, Bellevue, WA (US); J. Nelson Wright, Mercer Island, WA (US); Steven C. Dimmer, Bellevue, WA (US); Lynn M. Purdy, Sammamish, WA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 1089 days.

(21) Appl. No.: 11/190,195

(22) Filed: Jul. 25, 2005

(65) Prior Publication Data

US 2006/0058648 A1    Mar. 16, 2006

Related U.S. Application Data

(60) Provisional application No. 60/590,525, filed on Jul. 23, 2004, provisional application No. 60/590,873, filed on Jul. 23, 2004, provisional application No. 60/590,872, filed on Jul. 23, 2004.

(51) Int. Cl.
*A61B 5/05* (2006.01)

(52) U.S. Cl. ......... 600/427; 600/424; 600/410; 600/407

(58) Field of Classification Search .................. None
See application file for complete search history.

(56) References Cited

U.S. PATENT DOCUMENTS

| | | | |
|---|---|---|---|
| 3,967,161 A | 6/1976 | Lichtblau | |
| 4,017,858 A | 4/1977 | Kuipers | |
| 4,023,167 A | 5/1977 | Wahlstrom | |
| 4,114,601 A | 9/1978 | Abels | |
| 4,123,749 A | 10/1978 | Hartmann et al. | |
| 4,127,110 A | 11/1978 | Bullara | |

(Continued)

FOREIGN PATENT DOCUMENTS

DE    19914455    10/2000

(Continued)

OTHER PUBLICATIONS

U.S. Appl. No. 10/416,827, David Krag.

(Continued)

*Primary Examiner* — Tse Chen
*Assistant Examiner* — Joel F Brutus
(74) *Attorney, Agent, or Firm* — Perkins Coie LLP

(57) ABSTRACT

An integrated radiation therapy process comprises acquiring first objective target data related to a parameter of a target within a patient by periodically locating a marker positioned within the patient using a localization modality. This method continues with obtaining second objective target data related to the parameter of the target by periodically locating the marker. The first objective target data can be acquired in a first area that is apart from a second area which contains a radiation delivery device for producing an ionizing radiation beam for treating the patient. The localization modality can be the same in both the first and second areas. In other embodiments, the first objective target data can be acquired using a first localization modality that uses a first energy type to identify the marker and the second objective target data can be obtained using a second localization modality that uses a second energy type to identify the marker that is different than the first energy type.

13 Claims, 6 Drawing Sheets

U.S. PATENT DOCUMENTS

| | | | |
|---|---|---|---|
| 4,160,971 | A | 7/1979 | Jones et al. |
| 4,222,374 | A | 9/1980 | Sampson et al. |
| 4,260,990 | A | 4/1981 | Lichtblau |
| 4,393,872 | A | 7/1983 | Reznik et al. |
| 4,466,075 | A | 8/1984 | Groch |
| 4,618,822 | A | 10/1986 | Hansen |
| 4,633,250 | A | 12/1986 | Anderson |
| 4,642,786 | A | 2/1987 | Hansen |
| 4,643,196 | A | 2/1987 | Tanaka et al. |
| 4,696,287 | A | 9/1987 | Hortmann et al. |
| 4,737,794 | A | 4/1988 | Jones |
| 4,795,995 | A | 1/1989 | Eccleston |
| 4,799,495 | A | 1/1989 | Hawkins |
| 4,849,692 | A | 7/1989 | Blood |
| 4,909,789 | A | 3/1990 | Taguchi et al. |
| 4,936,823 | A | 6/1990 | Colvin et al. |
| 4,945,305 | A | 7/1990 | Blood |
| 4,945,914 | A * | 8/1990 | Allen .............................. 600/426 |
| 4,994,079 | A | 2/1991 | Genese |
| 5,031,634 | A | 7/1991 | Simon |
| 5,050,608 | A | 9/1991 | Watanabe |
| 5,062,847 | A | 11/1991 | Barnes |
| 5,095,224 | A | 3/1992 | Renger |
| 5,099,845 | A | 3/1992 | Besz |
| 5,107,862 | A | 4/1992 | Fabian et al. |
| 5,117,829 | A * | 6/1992 | Miller et al. .................. 600/427 |
| 5,142,292 | A | 8/1992 | Chang |
| 5,170,055 | A | 12/1992 | Carroll et al. |
| 5,188,368 | A | 2/1993 | Ryan |
| 5,198,877 | A | 3/1993 | Schulz |
| 5,221,269 | A | 6/1993 | Miller |
| 5,222,499 | A * | 6/1993 | Allen et al. .................... 600/426 |
| 5,240,011 | A | 8/1993 | Assa |
| 5,325,873 | A | 7/1994 | Hirschi |
| 5,353,804 | A | 10/1994 | Kornberg et al. |
| 5,377,678 | A | 1/1995 | Dumoulin |
| 5,397,329 | A | 3/1995 | Allen |
| 5,409,004 | A | 4/1995 | Sloan |
| 5,411,026 | A | 5/1995 | Carol |
| 5,417,210 | A | 5/1995 | Funda |
| 5,423,334 | A | 6/1995 | Jordan |
| 5,425,367 | A | 6/1995 | Shapiro |
| 5,425,382 | A | 6/1995 | Golden |
| 5,446,548 | A | 8/1995 | Gerig |
| 5,453,686 | A | 9/1995 | Anderson |
| 5,509,900 | A | 4/1996 | Kirkman |
| 5,515,853 | A | 5/1996 | Smith |
| 5,526,812 | A | 6/1996 | Dumoulin |
| 5,528,651 | A | 6/1996 | Leksell |
| 5,546,951 | A | 8/1996 | Ben-Haim |
| 5,558,091 | A | 9/1996 | Acker |
| 5,568,809 | A | 10/1996 | Ben-haim |
| 5,572,999 | A | 11/1996 | Funda |
| 5,617,857 | A | 4/1997 | Chader |
| 5,622,170 | A | 4/1997 | Schulz |
| 5,622,187 | A | 4/1997 | Carol |
| 5,629,967 | A | 5/1997 | Leksell |
| 5,630,431 | A | 5/1997 | Taylor |
| 5,638,819 | A | 6/1997 | Manwaring et al. |
| 5,680,106 | A | 10/1997 | Schrott |
| 5,681,326 | A | 10/1997 | Lax |
| 5,697,384 | A | 12/1997 | Miyawaki et al. |
| 5,707,362 | A | 1/1998 | Yoon |
| 5,707,390 | A | 1/1998 | Bonutti |
| 5,727,552 | A | 3/1998 | Ryan |
| 5,735,795 | A | 4/1998 | Young et al. |
| 5,745,545 | A | 4/1998 | Hughes |
| RE35,816 | E | 6/1998 | Schulz |
| 5,764,052 | A | 6/1998 | Renger |
| 5,769,861 | A | 6/1998 | Vilsmeier |
| 5,779,638 | A | 7/1998 | Vesely |
| 5,797,849 | A | 8/1998 | Vesely |
| 5,805,661 | A | 9/1998 | Leksell |
| 5,810,851 | A | 9/1998 | Yoon |
| 5,815,076 | A | 9/1998 | Herring |
| 5,817,022 | A | 10/1998 | Vesely |
| 5,820,553 | A | 10/1998 | Hughes |
| 5,823,192 | A | 10/1998 | Kalend |
| 5,828,770 | A | 10/1998 | Leis |
| 5,830,144 | A | 11/1998 | Vesely |
| 5,840,148 | A | 11/1998 | Campbell |
| 5,868,673 | A | 2/1999 | Vesely |
| 5,868,675 | A | 2/1999 | Henrion |
| 5,879,297 | A | 3/1999 | Haynor |
| 5,879,357 | A | 3/1999 | Heaton |
| 5,899,857 | A * | 5/1999 | Wilk .............................. 600/407 |
| 5,902,238 | A | 5/1999 | Golden |
| 5,902,310 | A | 5/1999 | Foerster |
| 5,910,144 | A | 6/1999 | Hayashi |
| 5,913,820 | A | 6/1999 | Bladen |
| 5,923,417 | A | 7/1999 | Leis |
| 5,928,137 | A | 7/1999 | Green et al. |
| 5,951,481 | A | 9/1999 | Evans |
| 5,987,349 | A | 11/1999 | Schulz |
| 5,989,265 | A | 11/1999 | Bouquet De La Joliniere et al. |
| 6,015,390 | A | 1/2000 | Krag |
| 6,019,725 | A | 2/2000 | Vesely |
| 6,026,818 | A | 2/2000 | Blair |
| 6,049,587 | A | 4/2000 | Leksell |
| 6,052,477 | A | 4/2000 | Wang |
| 6,059,734 | A | 5/2000 | Yoon |
| 6,061,644 | A | 5/2000 | Leis |
| 6,064,904 | A | 5/2000 | Yanof |
| 6,067,465 | A | 5/2000 | Foo |
| 6,076,008 | A | 6/2000 | Bucholz |
| 6,081,238 | A | 6/2000 | Alicot |
| 6,082,366 | A | 7/2000 | Andra et al. |
| 6,094,007 | A | 7/2000 | Faul |
| 6,097,994 | A | 8/2000 | Navab |
| 6,144,875 | A * | 11/2000 | Schweikard et al. ......... 600/427 |
| 6,161,009 | A * | 12/2000 | Skurdal et al. ................ 455/423 |
| 6,173,715 | B1 | 1/2001 | Sinanan |
| 6,198,963 | B1 | 3/2001 | Haim et al. |
| 6,239,724 | B1 | 5/2001 | Doron |
| 6,246,900 | B1 | 6/2001 | Cosman et al. |
| 6,307,473 | B1 | 10/2001 | Zampini et al. |
| 6,363,940 | B1 | 4/2002 | Krag |
| 6,371,379 | B1 | 4/2002 | Dames |
| 6,381,485 | B1 * | 4/2002 | Hunter et al. ................. 600/407 |
| 6,401,722 | B1 | 6/2002 | Krag |
| 6,405,072 | B1 * | 6/2002 | Cosman ....................... 600/426 |
| 6,416,520 | B1 | 7/2002 | Kynast et al. |
| 6,474,341 | B1 | 11/2002 | Hunter |
| 6,497,358 | B1 | 12/2002 | Walsh |
| 6,675,810 | B2 | 1/2004 | Krag |
| 6,698,433 | B2 | 3/2004 | Krag |
| 6,812,842 | B2 | 11/2004 | Dimmer |
| 6,822,570 | B2 | 11/2004 | Dimmer et al. |
| 6,838,990 | B2 | 1/2005 | Dimmer |
| 6,918,919 | B2 | 7/2005 | Krag |
| 7,135,978 | B2 | 11/2006 | Gisselberg et al. |
| 2002/0065461 | A1* | 5/2002 | Cosman ....................... 600/426 |
| 2002/0193685 | A1* | 12/2002 | Mate et al. .................... 600/424 |
| 2003/0088178 | A1 | 5/2003 | Owens et al. |
| 2003/0192557 | A1 | 10/2003 | Krag et al. |
| 2003/0206614 | A1 | 11/2003 | Kendrick et al. |
| 2004/0092815 | A1* | 5/2004 | Schweikard et al. ......... 600/425 |
| 2004/0123871 | A1 | 7/2004 | Wright et al. |
| 2004/0125916 | A1 | 7/2004 | Herron et al. |
| 2004/0133101 | A1 | 7/2004 | Mate et al. |
| 2004/0138555 | A1 | 7/2004 | Krag et al. |
| 2004/0158146 | A1 | 8/2004 | Mate et al. |
| 2004/0176931 | A1 | 9/2004 | Wright et al. |
| 2005/0059884 | A1 | 3/2005 | Krag |
| 2005/0154280 | A1 | 7/2005 | Wright et al. |
| 2005/0154293 | A1 | 7/2005 | Gisselberg et al. |
| 2005/0195084 | A1 | 9/2005 | Dimmer et al. |
| 2005/0261570 | A1 | 11/2005 | Mate et al. |
| 2006/0074301 | A1 | 4/2006 | Meier et al. |
| 2006/0074302 | A1 | 4/2006 | Meier et al. |
| 2006/0079764 | A1 | 4/2006 | Wright et al. |

FOREIGN PATENT DOCUMENTS

| | | |
|---|---|---|
| EP | 0531081 A1 | 3/1993 |
| EP | 0 719 420 | 11/1999 |
| EP | 1 034 738 | 9/2000 |
| FR | 2635259 | 2/1990 |

| | | |
|---|---|---|
| FR | 2686499 | 7/1993 |
| JP | 8-166446 | 6/1996 |
| WO | WO-88/08282 | 11/1988 |
| WO | WO-95/25475 | 9/1995 |
| WO | WO-95/33519 | 12/1995 |
| WO | WO-96/08208 | 3/1996 |
| WO | WO-96/08999 | 3/1996 |
| WO | WO-97/12553 | 4/1997 |
| WO | WO-97/36192 | 10/1997 |
| WO | WO-97/48438 | 12/1997 |
| WO | WO-98/30166 | 7/1998 |
| WO | WO-98/38908 | 9/1998 |
| WO | WO-98/40026 A | 9/1998 |
| WO | WO-99/17133 | 4/1999 |
| WO | WO-99/27839 | 6/1999 |
| WO | WO-99/30182 | 6/1999 |
| WO | WO-99/33406 | 7/1999 |
| WO | WO-99/35966 | 7/1999 |
| WO | WO-99/40869 | 8/1999 |
| WO | WO-99/58044 | 11/1999 |
| WO | WO-99/58055 | 11/1999 |
| WO | WO-99/58065 | 11/1999 |
| WO | WO-00/24332 | 5/2000 |
| WO | WO-00/38579 | 7/2000 |
| WO | WO-00/51514 | 9/2000 |
| WO | WO-00/53115 | 9/2000 |
| WO | WO-00/65989 A | 11/2000 |
| WO | WO-01/34049 | 5/2001 |
| WO | WO-01/54765 | 8/2001 |
| WO | WO-02/09588 | 2/2002 |
| WO | WO-02/19908 | 3/2002 |
| WO | WO-02/39917 | 5/2002 |
| WO | WO-02/39918 | 5/2002 |
| WO | WO-02/100485 | 12/2002 |

OTHER PUBLICATIONS

International Search Report and Written Opinion for International Application No. PCT/US2005/026447; Calypso Medical Technologies, Inc; May 3, 2006; 18 pgs.

Hsiao, K., "Fast Multi-Axis Tracking of Magnetically-Resonant Passive Tags: Methods and Applications," Feb. 2001, Massachusetts Institute of Technology, Dept. of Electrical Engineering and Computer Science.

* cited by examiner

INTEGRATED RADIATION THERAPY SYSTEMS AND METHODS FOR TREATING A TARGET IN A PATIENT

CROSS-REFERENCE TO RELATED APPLICATIONS

The present application claims the benefit of U.S. Patent Application Nos. 60/590,525; 60/590,873; and 60/590,872; all of which were filed on Jul. 23, 2004, and are herein incorporated by reference in their entirety.

U.S. patent application Ser. No. 09/877,498 filed Jun. 5, 2002, and Ser. No. 11/166,801 filed Jun. 24, 2005, are incorporated herein by reference in their entirety.

TECHNICAL FIELD

This invention relates generally to radiation therapy and more particularly to systems and methods that integrate patient assessment, treatment planning, simulation, setup, treatment and/or verification procedures to enhance the efficiency and efficacy of the therapy.

BACKGROUND OF THE INVENTION

Cancer is a disease that begins in the cells of a patient. The typical treatments for cancer include surgery, radiation, and/or chemotherapy. Because cancer varies from person to person, no single treatment may be effective for all patients. Typical surgeries for treating cancer include cutting, ablating, or otherwise removing an entire body part or just a portion of a body part where the cancer is located. Surgery, however, is not a viable option for many patients because of the location and/or type of cancer. Surgical treatments may also result in complications with anesthesia or infection, and surgical treatments may have long, painful recovery periods. Chemotherapy involves chemically treating the cancer. Chemotherapy is not a desirable option for several types of cancers and it can also have many complications.

Radiation therapy has become a significant and highly successful process for treating prostate cancer, lung cancer, brain cancer and many other types of localized cancers. Radiation therapy procedures generally involve (a) assessing the patient to determine a radiation prescription, (b) developing a treatment plan to carry out the prescribed radiation (e.g., dose, beam shape, beam angle, pulse width, etc.), (c) simulating treatment according to the treatment plan, (d) setting up a treatment session by positioning the patient in a radiation vault such that the target is at a desired location relative to the radiation beam, (e) treating the patient in one or more radiation sessions (i.e., radiation fractions) to irradiate the cancer, and (f) verifying or otherwise managing the treatment process to assess and modify the radiation sessions. Many radiation therapy procedures require several radiation fractions over a period of approximately 5-45 days. As such, many aspects of these procedures are repeated over this period and each procedure generates a significant amount of data.

To further improve the treatment of localized cancers with radiation therapy, it is generally desirable to increase the radiation dose because higher doses are more effective at destroying most cancers. Increasing the radiation dose, however, also increases the potential for complications to healthy tissues. The efficacy of radiation therapy accordingly depends on both the total dose of radiation delivered to the tumor and the total dose of radiation delivered to normal tissue adjacent to the tumor. To avoid damaging normal tissue adjacent to the tumor, the radiation should be prescribed to a tight treatment margin around the target such that only a small volume of healthy tissue is irradiated. For example, the treatment margin for prostate cancer should be selected to avoid irradiating rectal, bladder and bulbar urethral tissues. Similarly, the treatment margin for lung cancer should be selected to avoid irradiating healthy lung tissue. Therefore, it is not only desirable to increase the radiation dose delivered to the tumor, but it also desirable to avoid irradiating healthy tissue.

One difficulty of radiation therapy is that the target often moves within the patient either during or between radiation sessions. For example, the prostate gland moves within the patient during radiation treatment sessions because bowel and/or bladder conditions (e.g., full or empty) displace soft tissue structures within the body. Respiration can also displace tumors in the prostate gland. Tumors in the lungs also move during radiation sessions because of respiration and cardiac functions (e.g., heartbeats and vasculature constriction/dialation). To compensate for such movement, the treatment margins are generally larger than desired so that the tumor remains in the treatment volume. This is not a desirable solution because larger treatment margins generally result in irradiating larger volumes of normal tissue.

Conventional radiation therapy procedures address the problem of target movement with extensive treatment planning, simulation, setup, and verification procedures. Conventional treatment planning procedures are performed outside of the radiation vault well before the first radiation fraction. For example, conventional planning procedures typically involve obtaining CT images of the tumor and implanted gold fiducials to determine the size, shape and orientation of the tumor. These initial CT images are often not sufficient for carrying out radiation treatments because they do not address the internal motion of the tumor. As a result, patients may also undergo a simulation procedure using a different CT scanner that correlates the CT images in a time sequence to reconstruct the three dimensional volume and movement of the tumor. Using this data, the treatment margins can be set based on the observed trajectory of the tumor within the patient.

Conventional treatment planning procedures can be relatively expensive, require sophisticated equipment and technicians, and restrict the throughput of patients. For example, CT scanners are very expensive machines that require dedicated rooms because they use an ionizing energy for imaging the tumor and the gold fiducials. Additionally, the CT scanners for obtaining the initial images are typically different than the CT scanners that are used in the simulation procedures such that two separate dedicated areas with very expensive machines are required in these applications. Another concern of conventional planning processes is that the technicians subjectively interpolate the location of the tumor and the gold fiducials from the CT scans. This requires additional time and expense for skilled personnel, and it is also subject to human error. Still another concern of conventional planning procedures is that shuttling patients from one area to another and accurately managing the information restricts patient throughput. This may result in under utilization of the expensive equipment, facilities, and personnel. Therefore, conventional treatment planning procedures need to be improved.

Conventional setup procedures for aligning the tumor with the isocenter of the radiation beam are also an area of concern because they can be time-consuming and subject to error. Current setup procedures generally align (a) external reference markings on the patient and/or (b) internal gold fiducials in the patient with desired coordinates of the radiation delivery device. For example, the approximate location of the tumor is determined relative to alignment points on the exterior of the patient and/or gold fiducials in the patient. During setup, the external marks and/or gold fiducials are aligned with a reference frame of the radiation delivery device to position the treatment target at the beam isocenter of the radiation beam (also referenced herein as the machine isocenter).

Conventional setup procedures using external marks may be inadequate because the target may move relative to the external marks between the patient planning procedure and the treatment session and/or during the treatment session. As such, the target may be offset from the machine isocenter even when the external marks are at predetermined locations for positioning the target at the machine isocenter.

Conventional setup procedures using internal gold fiducials are also generally inadequate because this is a time-consuming process that may produce inaccurate results. In a typical setup procedure using gold fiducials, a technician positions the patient on a movable table in the radiation vault. The technician then leaves the room and operates an X-ray machine to acquire stereotactic X-rays of the target area. From these X-rays, an offset amount for moving the patient is determined. The technician then moves the table by the offset amount and acquires a second set of stereotactic X-rays to confirm that the position of the tumor is at the machine isocenter. This process may need to be repeated if the first sequence did not achieve the required placement. This process is time-consuming and may be unpleasant for the patient because the technician must vacate the radiation vault while the X-rays are acquired. This procedure may also be inaccurate because the patient may inadvertently move after taking the stereotactic X-rays such that the tumor is not at the location in the images. The potential inaccuracy of this process may be exacerbated because a person typically determines the offset by subjectively interpolating the CT images. Therefore, conventional setup procedures using gold fiducials tie up expensive linear accelerators in the radiation vault for extensive periods of time just to position patients for treatment, and conventional setup procedures may be inaccurate.

Another aspect of current radiation therapy techniques is to verify the performance of the radiation fraction and assess the status of the tumor for managing subsequent treatment fractions. Conventional verification systems record the status of the hardware of the radiation delivery device during a radiation session. For example, conventional verification systems record the beam intensity, beam position, and collimator configuration at time intervals during a radiation fraction. The hardware information from the radiation delivery device is then used to estimate the radiation dosage delivered to discrete regions of the tumor. Such conventional verification procedures, however, are subject to errors because the tumor is assumed to be at the machine isocenter throughout the radiation fraction. Moreover, the tumor is generally assumed to have the same size, shape and trajectory as determined in the planning procedure. The actual dosage delivered to the tumor may be significantly different because the tumor typically moves during the radiation fraction, or the tumor may have changed shape or trajectory after several radiation fractions because of the effects of the radiation. In conventional radiation therapy systems, the changes in shape or trajectory of the tumor can be determined using additional CT scans, but this requires additional time and use of expensive CT scanners and personnel. CT scans also expose the patient to more radiation. Therefore, conventional verification procedures can also be improved.

Another challenge of providing radiation therapy is that the information from the planning, simulation, setup, treatment, and verification procedures is typically generated from different equipment in various formats. Each stage of the process typically uses a stand-alone system that has unique formats/protocols that do not communicate with systems used at other stages of the process. This is inefficient because managing the data from the different procedures in a coherent, integrated manner may be difficult. For example, information from the CT scans, treatment plans, and the radiation sessions may be generated from equipment that uses different formats and/or protocols that are not compatible with each other. The information may accordingly need to be managed using some manual input or control. As such, expensive equipment and highly trained technicians are often under utilized because information is not readily available.

DETAILED DESCRIPTION

A. Overview

Figure 1:
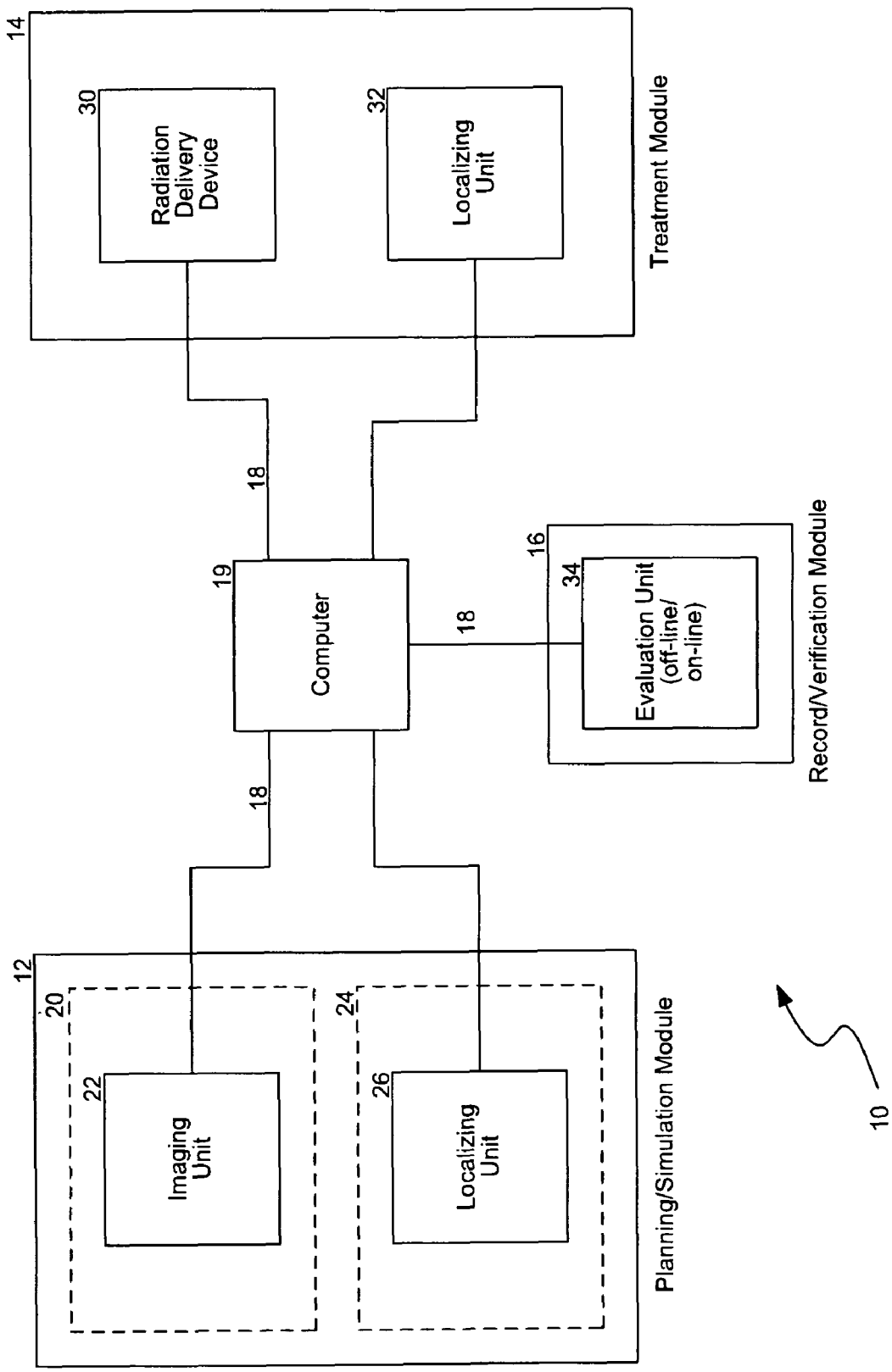
FIG. 1 is a schematic diagram illustrating an integrated system for radiation therapy in accordance with an embodiment of the invention.

FIGS. 1-6 illustrate specific embodiments of systems and methods for integrating radiation therapy procedures in accordance with the invention. These embodiments of the systems and methods are generally described with respect to localizing units that periodically locate a marker positioned within a patient with respect to an external reference frame outside of the patient. For example, the localizing units can use a wirelessly transmitted magnetic field and a marker with a transponder that wirelessly transmits location signals in response to the magnetic field. It will be appreciated that this type of localizing unit uses non-ionizing magnetic energy to locate the marker, but that other types of non-ionizing energy, such as ultrasound, RF, etc., may also be used in some circumstances. Several embodiments of the invention may also image or otherwise identify the markers using an ionizing energy in conjunction with or in lieu of periodically localizing the markers using a non-ionizing energy.

In several embodiments, the integrated systems localize at least one implanted marker during several different stages of the therapy process to provide objective target data in a common format that can be communicated and used throughout the implanting, planning, simulation, setup, treatment, and verification procedures. The objective target data can also be used for modifying any of these procedures. Several embodiments of the integrated methods and systems implant or otherwise position a marker within the patient and track the marker using a non-ionizing energy throughout substantial portions of the process by periodically locating the marker.

Several such markers are generally tracked when the patient is in the radiation vault and/or other areas of a facility by localizing units that periodically locate the markers in an external reference frame. The tracked locations of the markers can be used to monitor and evaluate the status of the target at many stages throughout the radiation therapy process without utilizing expensive equipment and rooms within the facility. As a result, the integrated methods and systems are expected to provide a high degree of efficiency and enhance the efficacy of radiation therapy.

One embodiment of an integrated process for treating a target in a patient comprises acquiring first target data by locating a marker in a reference frame external to the patient using a marker localization modality. The marker is positioned within a patient relative to a target that is to be irradiated or otherwise treated with an ionizing radiation beam. This method continues with obtaining second target data by locating the marker using the marker localization modality while the patient is at a radiation delivery device that produces the ionizing radiation beam. Additional stages of this method include irradiating the patient with the ionizing radiation beam while obtaining the second target data using the marker localization modality, acquiring hardware data related to the radiation delivery device, and evaluating the radiation delivered to the patient using the first target data, the second target data, and/or the hardware data. The external reference frame in which the first target data is located can be any reference frame that is external to the patient. For example, the external reference frame can be based on a sensor array or other type of device positioned outside of the patient that acquires signals or other information related to the position of the marker relative to the outside device. The external reference frame can alternatively be a reference frame in a room or other fixed reference frame outside of the patient. The marker localization modality for acquiring the first target data and obtaining the second target data typically uses the same type of energy for acquiring the target data. For example, the energy could be an ionizing energy (e.g., kilovoltage or megavoltage X-rays) or a non-ionizing radiation (magnetic, ultrasound, or other suitable electromagnetic radiation). The hardware data related to the radiation delivery device can include data regarding the position, presence or other attribute of the table supporting the patient, the gantry position, any aspect related to the radiation beam, accessories that are used on and/or around the patient, and any other device in the radiation vault associated with the radiation delivery device.

Another embodiment of an integrated radiation therapy process comprises acquiring first objective target data related to a parameter of a target within a patient by periodically locating a marker positioned within the patient using a localization modality located in a first area. The first area, for example, is apart from a second area that contains a radiation delivery device which produces an ionizing radiation beam for treating the patient. This method continues with obtaining second objective target data related to the parameter of the target by periodically locating the marker using the localization modality in the second area.

Another embodiment of an integrated radiation therapy process comprises acquiring first objective target data related to a parameter of a target within a patient by periodically locating a marker positioned within the patient using a first localization modality that uses a first energy type to identify the marker. This method continues with obtaining second objective target data related to the parameter of the target by periodically locating the marker using a second localization modality that uses a second energy type to identify the marker that is different than the first energy type. For example, the marker can be identified in a CT scan or other type of X-ray using a first localization modality that uses ionizing energy to identify the marker. The second objective target data can be obtained by using a second localization modality that uses a magnetic field to identify the same marker either concurrently with acquiring the first objective target data or at a different point in time.

Another embodiment of a method of integrated radiation therapy comprises acquiring objective planning data related to a parameter of a target within a patient by periodically locating a marker positioned within the patient using a localization modality. This method continues with obtaining objective in-situ data related to the parameter of the target by periodically locating the marker with the localization modality while the patient is at a radiation delivery device that produces the ionizing radiation beam. This method further includes determining a parameter of the radiation delivered to the patient using the in-situ data.

Another embodiment of a method of integrated radiation therapy comprises performing a treatment planning procedure, performing a set up procedure, and performing a radiation treatment fraction. The treatment planning procedure includes (a) obtaining images of a target within a patient and of a marker positioned within the patient proximate to the target using an imaging modality, (b) acquiring first target data by periodically locating the marker with respect to a reference frame external to the patient using a localization modality, and (c) developing a treatment plan using the images and the first target data. The marker can be located using the localization modality before, during, and/or after obtaining the images of the target and marker. The set up procedure includes (a) determining locations of the marker with respect to a machine isocenter of a radiation delivery device by periodically locating the marker in a radiation vault containing the radiation delivery device using the localization modality, and (b) moving the patient to align the target relative to the machine isocenter based on the determined locations of the marker. The radiation treatment fraction includes irradiating the patient according to the treatment plan while periodically locating the marker in the radiation vault using the localization modality.

Still another embodiment of a method of integrated radiation therapy comprises acquiring objective planning data related to a parameter of the target within a patient by periodically locating a marker positioned within the patient using a portable localization system at a treatment planning area. This method further includes moving the portable localization system to a radiation vault containing a radiation delivery device separate from the treatment planning area, and determining locations of the marker with respect to a machine isocenter of the radiation delivery device by periodically locating the marker in the radiation vault using the portable localizing system.

A further aspect of the present invention is directed toward methods for treating a target within a patient using radiation therapy. One embodiment of such a method includes developing a treatment plan for controlling a radiation delivery device to treat a target with a beam of radiation, and operating the radiation delivery device according to the treatment plan to irradiate the target. This method further includes periodically locating a marker positioned within the patient with a localization system using non-ionizing energy to determine locations of the marker in a reference frame external to the patient, and determining a parameter of the target based on the locations of the marker in the reference frame. This method also includes adapting and/or confirming the treatment plan based at least in part on the determined parameter of the target.

Another aspect of the invention is directed toward methods for establishing systems for radiation therapy. One embodiment of such a method includes providing a first node having a first localizing unit located in a first area of a facility, providing a second node having a second localizing unit located in a radiation vault containing a radiation delivery device, and operatively coupling the first node to the second node by a network to transfer target data between the first and second nodes. The first localizing unit at the first node, for example, is configured to locate a marker positioned within the patient with respect to a reference frame external to the patient. The second localizing unit of the second node, is configured to locate the marker positioned within the patient with respect to a reference frame of the radiation delivery device.

Additional aspects of the invention are directed toward systems for radiation therapy. One embodiment of such a system comprises a first node having a first localizing unit located in a first area of a facility, a second node having a second localizing unit located in a radiation vault containing a radiation delivery device, and a network operatively coupling the first node to the second node to transfer target data between the first and second nodes. The first localizing unit is configured to locate a marker positioned within the patient with respect to a reference frame external to the patient. The second localizing unit is configured to locate the marker positioned within the patient with respect to a reference frame of the radiation delivery device.

Another embodiment of a method for integrated radiation therapy comprises acquiring first objective target data related to a parameter of a target by tracking markers implanted in the patient using a tracking modality located in a first area of a facility. This method can continue by obtaining second objective target data related to the parameters of the target by tracking the markers using the same tracking modality in a second area of the facility that contains a radiation delivery device. For example, the first objective target data can be obtained by tracking the markers using an alternating magnetic field in an observation area of the facility, and the second objective target data can be obtained using the same localizing unit or a similar localizing unit that uses an alternating magnetic field in the radiation vault. The objective target data can include the relative locations between the markers and/or the locations of the markers relative to a machine isocenter in the radiation vault. As such, the configuration of the target, the trajectory of the target, and/or the location of the target relative to the machine isocenter can be determined throughout the facility and while a technician is present with the patient.

Another aspect of integrated radiation therapy is a method for developing a treatment plan for treating a target within a patient. An embodiment of this method includes tracking markers implanted in the patient with a localizing system using non-ionizing energy to determine locations of the markers in a reference frame. This method can further include determining a physical parameter of the target within the patient based on the locations of the markers in the reference frame. The physical parameter, for example, can be the target configuration and/or the target trajectory.

Still another aspect of integrated radiation therapy is a method for integrating planning and treatment procedures. One embodiment, for example, includes positioning a target relative to a machine isocenter in a radiation vault containing a radiation delivery machine. The desired location of the target is defined by the treatment plan. After positioning the target, this method proceeds by irradiating the patient with a radiation beam from the radiation delivery device. This method also includes tracking locations of markers implanted within the patient for at least a substantial portion of the time while the patient is being positioned and/or irradiated in the radiation vault.

Several of the procedures described below with reference to FIGS. 1-6 may have additional steps or stages, and other embodiments of the invention may not include some of the steps/stages illustrated in FIGS. 1-6. Additionally, other embodiments of systems and methods for integrating radiation therapy in accordance with the invention are described and/or claimed, but not necessarily illustrated in FIGS. 1-6. A person skilled in the art, however, will understand that the invention may be practiced without several of the details shown and described with reference to FIGS. 1-6, or that additional details can be added to the invention. Where the context permits, singular or plural terms may also include the plural or singular term, respectively. Moreover, unless the word "or" is expressly limited to mean only a single item exclusive from other items in reference to a list of at least two items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same features and/or types of other features and components are not precluded.

B. Embodiments of Integrated Radiation Systems

FIG. 1 schematically illustrates an integrated system 10 for radiation therapy including a planning/simulation module 12, a treatment module 14, and a record/verification module 16. In the embodiment shown in FIG. 1, the planning/simulation module 12, treatment module 14, and record/verification module 16 are located in separate areas of a facility. In other embodiments, the record/verification module 16 can be located with the planning/simulation module 12 or treatment module 14. The planning/simulation module 12, treatment module 14, and verification module 16 can each have a computer, and these modules can be operatively coupled together by a network 18. The integrated system 10 can also include a separate computer 19 either in lieu of or in addition to the computers in each of the individual modules. The computer 19, for example, can be a central information system that manages the data from imaging units (CT scanners), localizing units, radiation delivery devices, and record/verification equipment. In alternative embodiments, a central information system can be part of one of the modules 12, 14 or 16 instead of a separate computer. As described in more detail below, the integrated system 10 provides objective target data from at least one of the modules that is stored, communicated, and/or used by at least one of the other modules to carry out the radiation therapy.

The planning/simulation module 12 in the embodiment illustrated in FIG. 1 includes an imaging area 20 containing an imaging unit 22 and an observation area 24 including a localizing unit 26. The imaging area 20 and the observation area 24 are typically separate rooms in a facility, but the localizing unit 26 and the imaging unit 22 can be in the same room. The imaging unit 22 uses an imaging modality that provides images showing tumors, lesions or other targets within the patient. CT imagers, for example, use ionizing energy to provide a three-dimensional representation of a tumor or other type of soft tissue lesion, and CT images also identify radiopaque markers implanted in the patient. The imaging unit can alternatively be an X-ray machine, magnetic resonance imaging (MRI) machine, or ultrasound system.

The imaging unit 22 can accordingly use ionizing radiation or non-ionizing radiation to acquire images of the target and the markers implanted in the patient.

The localizing unit 26 tracks at least one marker positioned within the patient using a localization modality. The localization modality of the localizing unit 26 is often different than the imaging modality of the imaging unit 22. The localizing unit 26, for example, can have a localization modality that uses a non-ionizing energy to periodically determine the locations of implanted markers relative to an external reference frame of the localizing unit or another external reference frame outside of the patient. The imaging unit 22, on the other hand, can have a localization modality that uses an ionizing energy to obtain X-rays or CT scans. Because the localizing unit 26 uses a non-ionizing localizing modality, other people can be proximate to the patient while the localizing unit 26 operates. The external reference frame in which the markers are located is any reference frame external to the patient. For example, the external reference frame can be a sensor or imaging array outside of the patient, or it can be a reference frame defined by a room or radiation delivery device.

The planning/simulation module 12 can further be used for performing a simulation procedure in the imaging area 20 and/or the observation area 24. A treatment plan is typically developed from at least the images obtained in the imaging unit 22, but the treatment plan may also include information from the localizing unit 26. The localizing unit 26, for example, can provide additional information for determining how to deliver the radiation prescribed for the patient based at least in part on the locations of the markers. In one embodiment, the radiation treatment is simulated using a series of CT images in a time sequence, or in another embodiment the treatment is simulated by periodically determining the locations of markers within the patient using the localizing unit either in lieu of or in addition to the CT images. As explained below, the results of the simulation procedure can be used to revise the treatment plan or provide additional information for the radiation treatments.

In one embodiment, the localizing unit 26 periodically locates or otherwise tracks small markers having transponders that produce magnetic fields in response to magnetic excitation fields at the resonant frequencies of the transponders. The localizing unit 26, for example, can include an excitation source that generates and wirelessly transmits the alternating magnetic excitation field to the implanted markers. The localizing unit 26 can further include a sensor assembly configured to receive a wirelessly transmitted location signal from the markers, a receiver for processing signals from the sensor assembly, and a computer for calculating the three-dimensional coordinates of the markers in a reference frame. Specific localizing units with magnetic localizers are described in the following U.S. patent applications, each of which is incorporated herein by reference in its entirety: U.S. patent application Ser. No. 10/344,700 filed Dec. 30, 2002; U.S. patent application Ser. No. 10/027,675 filed Dec. 20, 2001; U.S. patent application Ser. No. 10/213,980 filed Aug. 7, 2002; U.S. patent application Ser. No. 10/679,801 filed Oct. 6, 2003; U.S. patent application Ser. No. 10/382,123 filed Mar. 4, 2003; U.S. patent application Ser. No. 10/746,888 filed Dec. 24, 2003; and U.S. patent application Ser. No. 10/749,478 filed Dec. 31, 2003.

The treatment module 14 is typically a radiation vault having a radiation delivery device 30 and a localizing unit 32. The radiation delivery device 30 is a linear accelerator or other type of device that uses ionizing radiation to destroy tumors or other types of targets. Suitable linear accelerators are manufactured by Varian Medical Systems, Inc. of Palo Alto, Calif.; Siemens Medical Systems, Inc. of Iselin, N.J. Oklahoma; Elekta Instruments, Inc. of Crawley, Okla.; or Mitsubishi Denki Kabushik Kaisha of Japan. Such linear accelerators can deliver conventional single-field or multi-field radiation therapy, 3D conformal radiation therapy (3D CRT), intensity modulated radiation therapy (IMRT), stereotactic radiotherapy, and tomotherapy. The radiation delivery device can deliver a gated, contoured, or shaped beam of ionizing radiation from a movable gantry to an area or volume at a fixed location in a reference frame relative to the radiation delivery device. The volume to which the ionizing radiation beam is directed is referred to as the machine isocenter.

The localizing unit 32 can be substantially the same as the localizing unit 26 used for treatment planning and/or simulation. In some applications, in fact, a portable localizing unit can be moved from the planning/simulation module 12 to the treatment module 14 such that only a single localizing unit is used in the integrated system 10. The localizing unit 32 determines the actual positions of the markers in real-time while setting the patient up in the radiation delivery device 30 and while irradiating the target with the ionizing radiation. More specifically, the localizing unit 32 periodically determines the three-dimensional coordinates of the markers in real-time throughout the patient setup process and/or while irradiating the patient. The real-time marker locations are objective data that can be used to determine objective target data for controlling the beam or positioning the patient for dynamic therapy. The marker locations and/or the corresponding target data derived from the marker locations can also be recorded for subsequent evaluation to verify whether the radiation therapy has proceeded according to the treatment plan. Specific aspects of real-time tracking are described in more detail in U.S. application Ser. No. 11/166,801 incorporated by reference above.

The record/verification module 16 includes an evaluation unit 34 that receives the objective target data from the localizing unit 32 and hardware data from the radiation delivery device 30. The evaluation unit 34 can receive the data from the treatment module either on-line during a treatment or off-line after performing a treatment. The evaluation unit 34 can also receive the data from the imaging unit 22 and the localizing unit 26 from the planning/simulation module 12. The verification module 16 can assess the performance of the radiation therapy to provide an early indicator of changes in the configuration of the target (e.g., size and/or shape), the trajectory of the target within the patient caused by internal target movement, the dosage of radiation applied to the target, and/or other parameters. One aspect of the integrated system 10 is that objective target data related to the marker locations determined by the localizing unit 32 can be (a) correlated with hardware data regarding the status of the radiation delivery device and/or (b) compared to objective target data from the localizing unit 26 to provide a significant amount of information for modifying the treatment plan or otherwise improving the efficacy of the radiation therapy process.

C. Embodiments of Integrated Radiation Therapy Methods

The general practice for treating cancers begins by assessing the patient to define the type of treatment. For example, a practitioner assesses the patient to determine whether surgery, chemotherapy and/or radiation is the best type of clinical treatment for the patient. If radiation therapy is selected as part of the clinical treatment plan, a radiation oncologist determines a radiation prescription for the patient. For example, the radiation oncologist prescribes the number of radiation fractions, dose, and other parameters of the radiation therapy. The radiation oncologist or another practitioner then educates the patient about the options for implementing the radiation therapy, the patient's role in effectuating the treatment, and the ramifications of radiation therapy. The patient is then enabled for carrying out the integrated processes of radiation therapy in accordance with several embodiments of the invention. For example, a patient can be enabled by implanting or otherwise positioning a marker within the patient that can be tracked or at least periodically located using the localizing units 26 and/or 32. These markers may also be identified in images using an ionizing radiation. One or more markers are usually positioned within the patient by (a) implanting the markers in the patient relative to the target, (b) incorporating a marker in a bite block that the patient clamps between his/her teeth, or (c) otherwise securing a marker within the patient such that the marker is not optically accessible via a direct line-of-sight from outside of the patient. After the patient has been enabled, the patient is ready for radiation therapy in accordance with several methods of the invention.

Figure 2:
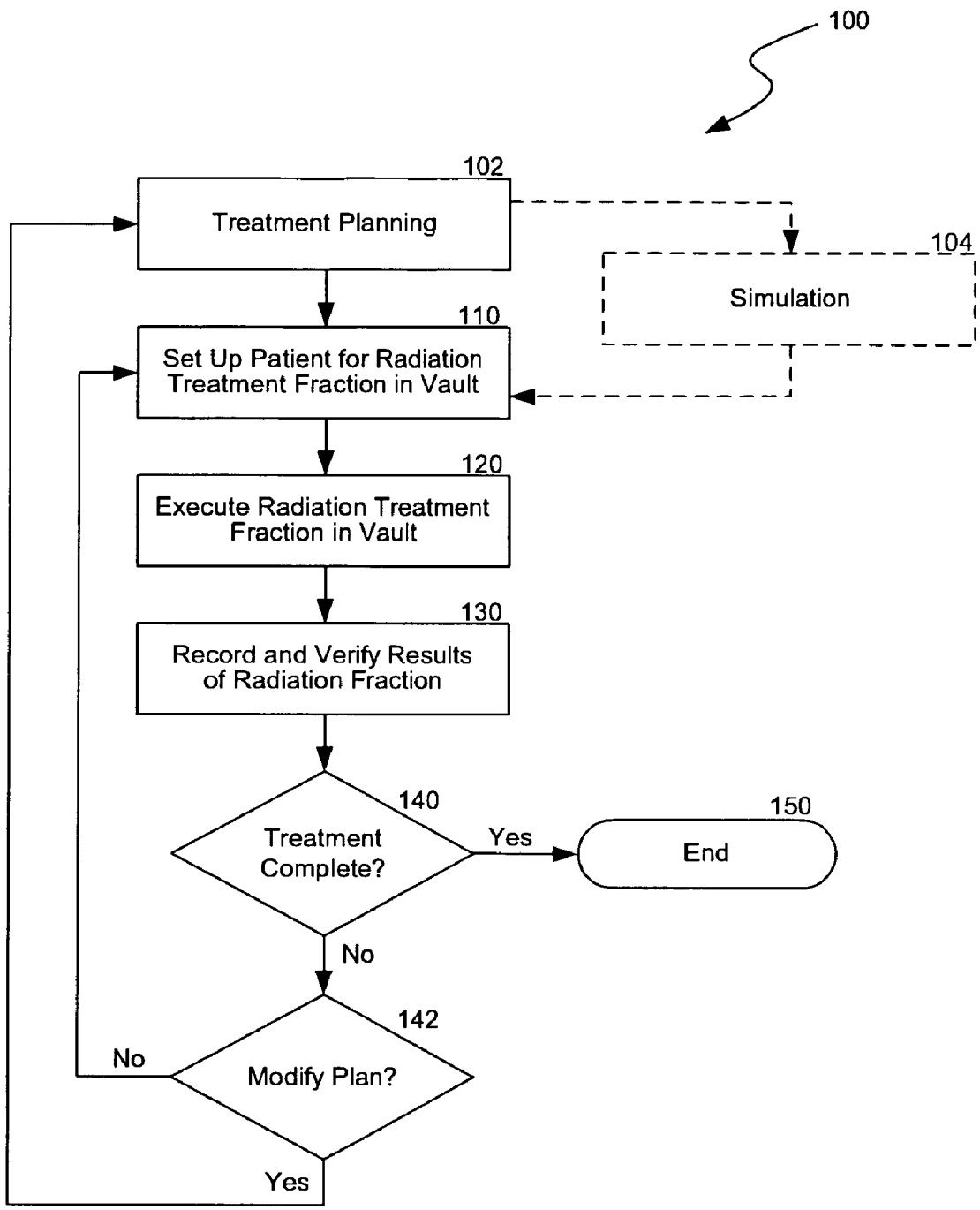
FIG. 2 is a flow diagram of an integrated process for radiation therapy in accordance with an embodiment of the invention.

FIG. 2 is a flow diagram of an integrated process 100 for radiation therapy in accordance with an embodiment of the invention. The integrated process 100 provides objective data that can be communicated and used at several nodes or modules throughout a facility. The integrated process 100 generally begins with a treatment planning process (Block 102) for determining how the radiation prescription will be effectuated. For example, the treatment planning process can include developing a model of a target within the patient and/or determining the radiation beam parameters of the treatment fractions. The treatment planning procedure, more specifically, can include obtaining images using a CT scanner or another suitable imaging modality that show the target configuration and the relative positions between the target and markers positioned within the patient. The coordinates of the target and of each marker relative to the external reference frame of the CT scanner are recorded and stored in a memory device. When the markers can be localized using a non-ionizing energy, it is possible that only a single CT scan may be necessary for developing a treatment plan and treating a patient. However, several CT scans will generally be used in most applications. Additional details of specific embodiments of the treatment planning procedure are described below with reference to FIG. 3.

Referring to FIG. 2, the integrated process 100 can optionally include a simulation procedure (Block 104) that simulates the treatment by monitoring the physical parameters of the target to confirm or modify the treatment plan. For example, the localizing unit 26 can track one or more markers positioned within the patient to determine the rotation and trajectory of the target while the patient undergoes a mock treatment in which the patient is positioned according to the treatment plan. The simulation procedure can further include training the patient using biofeedback responses so that the patient learns to breath or otherwise control his/her body in a manner that provides better control of the treatment margins and other parameters. As explained in more detail below with reference to FIG. 3, the simulation procedure can be performed before, during and/or after developing the treatment plan to provide more information for developing or modifying the treatment plan.

Referring to FIG. 2, the integrated process 100 further includes a setup procedure (Block 110) that includes positioning the patient in the radiation vault so that the target is at a desired location with respect to the machine isocenter of the radiation delivery device 30 (FIG. 1). The setup procedure is performed when the patient is on a support table in the radiation vault at the beginning of each radiation session. The localizing unit 32 (FIG. 1) (a) tracks or otherwise locates the markers periodically and (b) computes an offset between the actual position of the target and the desired position of the target for radiation treatment. In manual applications, a technician then moves the support table according to the calculated offset and verifies that the target is at the desired location using the localizing unit 32. In automatic applications, the localizing unit 32 sends a signal to the computer 19 (FIG. 1) or directly to the radiation delivery device 30 that causes the radiation delivery device 30 to move the table according to the calculated offset until the target is positioned at the desired target location with respect to the machine isocenter. In either application, the technician can be in the room with the patient while the markers are localized. This is expected to significantly reduce the setup time because the technician does not need to leave the room to determine the location of the target with respect to the machine isocenter as is currently required by conventional systems that use an ionizing radiation for positioning the patient. Several specific embodiments of the setup procedure are described in greater detail with reference to FIG. 4.

The integrated process 100 continues with a treatment procedure (Block 120) in which the patient is irradiated with a radiation beam from the radiation delivery device 30. The treatment procedure is typically a single treatment fraction that delivers a portion of the total planned radiation dosage. Many integrated radiation therapy processes require several treatment fractions to provide the desired dosage to the target. Several details of the treatment procedure are also described in greater detail below with reference to FIG. 4.

The integrated radiation therapy method 100 further includes a treatment management and verification procedure (Block 130) that quantifies the results of the radiation fractions, assesses whether the patient has been irradiated according to the treatment plan, and/or provides information for modifying the plan when appropriate. In the verification procedure, the evaluation unit 34 (FIG. 1) receives hardware data from the radiation delivery device 30 or other device related to the radiation delivery device. The evaluation unit 34 can also receive objective target data, such as location information of the target and/or markers from the localizing units 26 and 32 via the network 18 (FIG. 1). The evaluation unit 34 can perform several functions. For example, the evaluation unit 34 can correlate the status of the radiation delivery device 30 with the recorded locations of the target over sequential time intervals of the treatment procedure. This correlation between the machine status and the target location can be used to determine the radiation dose applied to discrete regions of the target and healthy tissue proximate to the target. The verification procedure can also determine other parameters of the target, such as the target configuration and target trajectory to provide an early indicator of whether the target has changed.

The integrated radiation therapy process 100 continues with a first decision (Block 140) and a second decision (Block 142). The first decision (Block 140) determines whether the treatment is complete. If the treatment is complete through all of the radiation fractions, then the process terminates at the end (Block 150). However, if the treatment is not complete, the process continues to the second decision (Block 142) which determines whether the treatment plan should be adapted to compensate for changes in the target, dosages delivered to discrete regions of the target, or other aspects of the treatment. If the current treatment plan is appropriate, the process 100 continues by repeating the setup procedure (Block 110), treatment procedure (Block 120), and verification procedure (Block 130) at the next radiation treatment session for the patient (typically one day or several days later). However, if the verification procedure indicates that the treatment plan should be changed, the integrated process 100 returns to the treatment planning procedure (Block 102) and/or the simulation procedure (Block 104) to redefine or otherwise adapt the treatment plan before proceeding with the setup and treatment procedures of the next radiation session.

The integrated process 100 illustrated in FIG. 2 provides several advantages compared to existing radiation therapy processes. For example, the objective target data from the localizing units 26 and 32 is communicated and used by the radiation delivery device 30 and the verification module 16. The integrated process 100 accordingly combines data from the planning/simulation module 12, the treatment module 14, and the verification module 16 in a manner that enables practitioners to more accurately assess the status of the tumor and more precisely position the tumor at the machine isocenter during therapy procedures.

The simulation procedure (Block 104) of the integrated process 100 also provides several advantages compared to existing simulation procedures that use CT scans. For example, the objective target data from the localizing unit 26 can be used to quickly determine the trajectory, rotation, shape, size and other parameters of the target without having to obtain images of the target using a CT scanner. The objective target data from the localizing unit 26 is expected to provide an accurate representation of the target parameters that does not rely on subjective interpretation of images. This is expected to enhance the accuracy of the simulation procedure. Additionally, because the localizing unit 26 uses a magnetic field or other type of non-ionizing energy to periodically locate the markers and determine the motion/configuration of the target, the simulation procedure does not need to use expensive CT scanners or subject the patient to additional radiation. Therefore, the simulation procedure of the integrated process 100 provides significant improvements over conventional simulation procedures.

Several embodiments of the integrated process 100 also efficiently use expensive imaging equipment and radiation delivery devices so that facilities can have a high patient throughput. One aspect of the localizing units 26 and 32 is that they frequently monitor the status of the target by continuously tracking implanted markers using non-ionizing radiation throughout much of the planning, setup, and treatment procedures. By tracking the markers in the normal course of the setup and treatment procedures, the status of the target can accordingly be monitored without rescanning the patient using the CT scanner. This allows the CT scanners and linear accelerators to be used solely for planning and treating patients, and it also provides early indicators of changes in the target (e.g., size/shape and trajectory). Moreover, because a technician can remain with the patient during the setup procedure and/or the setup procedure can be automated, the setup procedure can be quite short to process more patients through the radiation vault. Therefore, the integrated process is expected to increase the efficiency of radiation therapy.

D. Specific Embodiments of Treatment Planning Procedures

Figure 3:
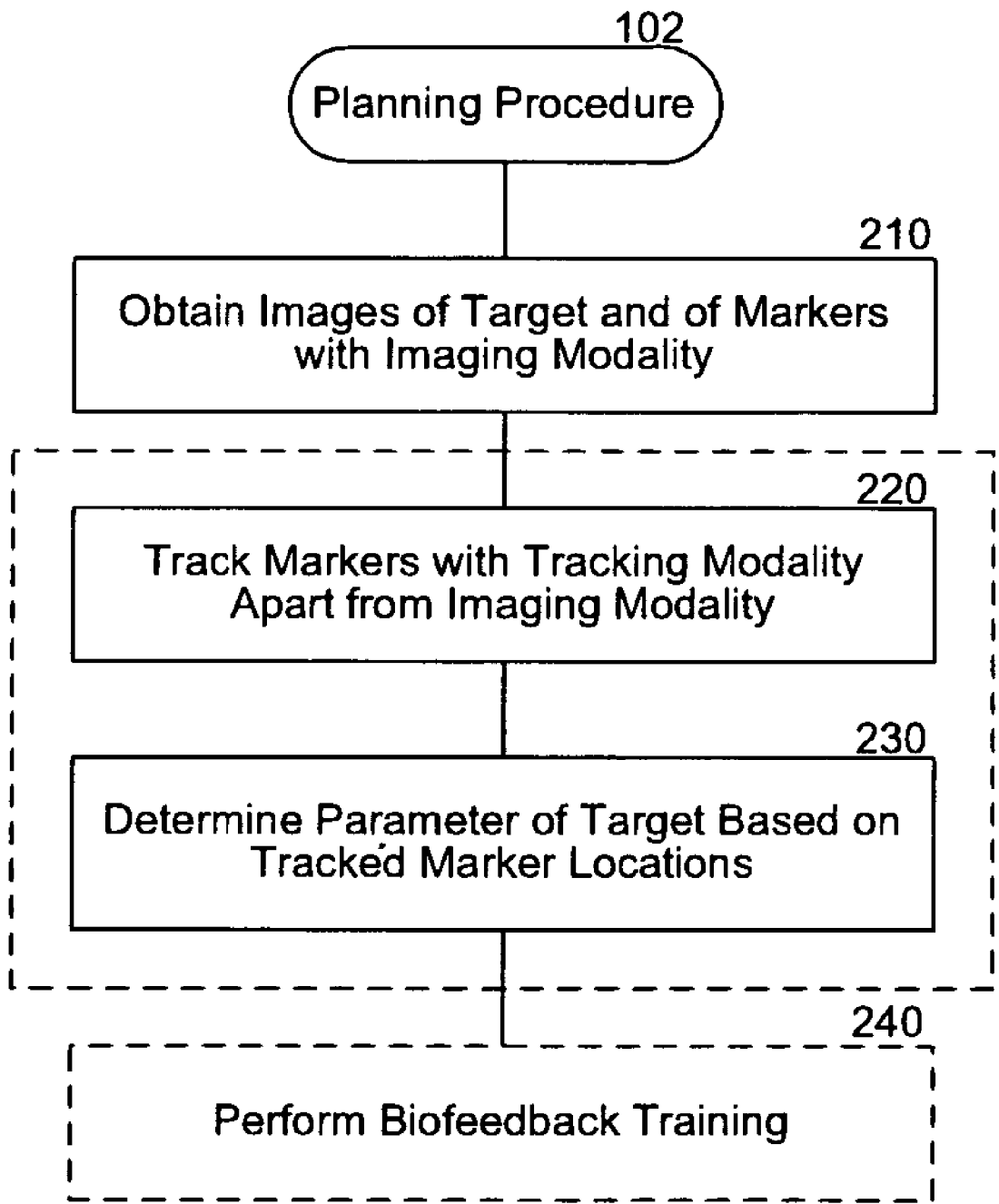
FIG. 3 is a flow diagram of a planning/simulation procedure performed as part of a radiation therapy process in accordance with an embodiment of the invention.

FIG. 3 is a flow diagram of a specific embodiment of the treatment planning procedure (FIG. 2, Block 102). In this embodiment, the treatment planning procedure includes an imaging stage 210 in which images of the tumor and implanted markers are obtained using CT scanners, ultrasound, MRI or other imaging modalities. As described above with reference to FIG. 1, the images are analyzed to determine the coordinates of the target and the markers in the external reference frame of the CT scanner. This data is then stored in memory for use in several other aspects of the treatment planning procedure, setup procedure (FIG. 2, Block 110), treatment procedure (FIG. 2, Block 120), and verification procedure (FIG. 2, Block 130). In the case of CT scanners, the imaging stage 210 further requires protecting the technician because the imaging modality of the CT scanners uses ionizing radiation to generate the images. As such, the imaging stage is generally performed at a separate area such as the imaging area 20 (FIG. 1). In some embodiments, the treatment planning procedure can be developed based on images obtained using ionizing energy or non-ionizing energy (e.g., ultrasound) without tracking the markers using the localizing unit 26. In other embodiments the treatment planning procedure also uses information generated by the localizing unit 26.

When information from the localizing unit is desired, the treatment planning procedure continues with a first tracking stage 220 in which the localizing unit 26 periodically locates at least one marker positioned within the patient with respect to an external reference frame. The localizing unit 26, for example, can continuously track at least one marker in real time to analyze the motion of the target, and/or it can track at least two markers in real time to characterize the size/shape of the target. The localizing unit uses a localization modality, and in several embodiments the localization modality uses a non-ionizing energy to periodically locate the markers. As explained above, the localizing unit 26 is preferably a magnetic localization system that can be used in virtually any observation area of the facility. For example, the observation area could be a lounge or a private cubicle where the markers can be tracked while the patient undergoes a simulation procedure or waits for the setup and treatment procedures. The tracking stage 220 acquires objective target data in addition to the imaging data by tracking the marker with a tracking modality that can be used in the radiation vault as well.

The treatment planning procedure can optionally include a target characterization/simulation stage 230 comprising determining parameters of the target using the objective target data from the localizing unit 26. The characterization/simulation stage 230 can also use images from the imaging stage 210. For example, one target parameter that can be monitored by tracking the markers is the configuration of the tumor. In this example, the size/shape of the tumor can be monitored by implanting at least two markers relative to the tumor and tracking the relative distances between the markers using a magnetic localization system. The target configuration defined by the initial relative positions between the markers is downloaded and stored in memory for comparison with subsequent measurements. If the size and/or shape of the target changes, then changes in the relative distances between the markers will correspond to changes in the target. The treatment plan can be modified or otherwise adapted based on changes in the marker configurations. Another parameter of the target that can be monitored by tracking the markers is the trajectory and/or rotation of the target within the patient. In many situations, the target will move along a trajectory within the patient because of respiration, bladder filling, or other reasons. The target trajectory within the patient can be ascertained by tracking the location of at least one marker over sequential time intervals using the localizing unit 26. The objective target data regarding the target trajectory can be downloaded and stored in memory for use in later processes.

The data provided by the target characterization/simulation stage 230 can be integrated into the treatment plan for use in the treatment module 14 and the verification module 16. For example, the trajectory of the target measured by the localizing unit 26 can be used to predict the internal movement of the target during the treatment procedure; this can then be used to determine the treatment margins and/or beam gating so that the target is located at a point where the target will reside in the path of the radiation beam. Another example is that the target configuration provided by the target characterization stage 230 can be used in subsequent comparisons to monitor changes in the target. If the size and/or shape of the target changes, a corresponding change will occur in the relative positions between the markers such that the treatment plan can be modified accordingly.

The treatment planning procedure generally uses information from stages 210, 220 and 230 to develop and refine a treatment plan. The imaging stage 210 provides initial images of the target, and the first tracking stage 220 and the characterization/simulation stage 230 provide objective target data that can be input into the plan. For example, the images obtained from the imaging stage 210, the objective target data obtained from the first tracking stage 220, and the data from the target characterization/simulation stage 230 can be used to determine the beam angle, collimator configuration, beam intensity, pulse width, table position, and gating operations of a treatment plan.

The treatment planning procedure can optionally include a biofeedback training stage 240. One embodiment of the biofeedback training stage 240 includes determining locations of the markers in a reference frame using the localizing unit 26 and instructing the patient to control a body function based upon the tracked locations of the markers. For example, while the localizing unit 26 tracks the markers, a computer can compute and display a representation of the trajectory of the target in real-time. The patient can watch the display and modulate his/her respiration to mitigate the target trajectory. As a result, the patient can be trained to proactively control body functions to maintain the target at the desired treatment location in the machine reference frame of the radiation delivery device 30 (FIG. 1).

E. Specific Embodiments of Setup and Treatment Procedures

Figure 4:
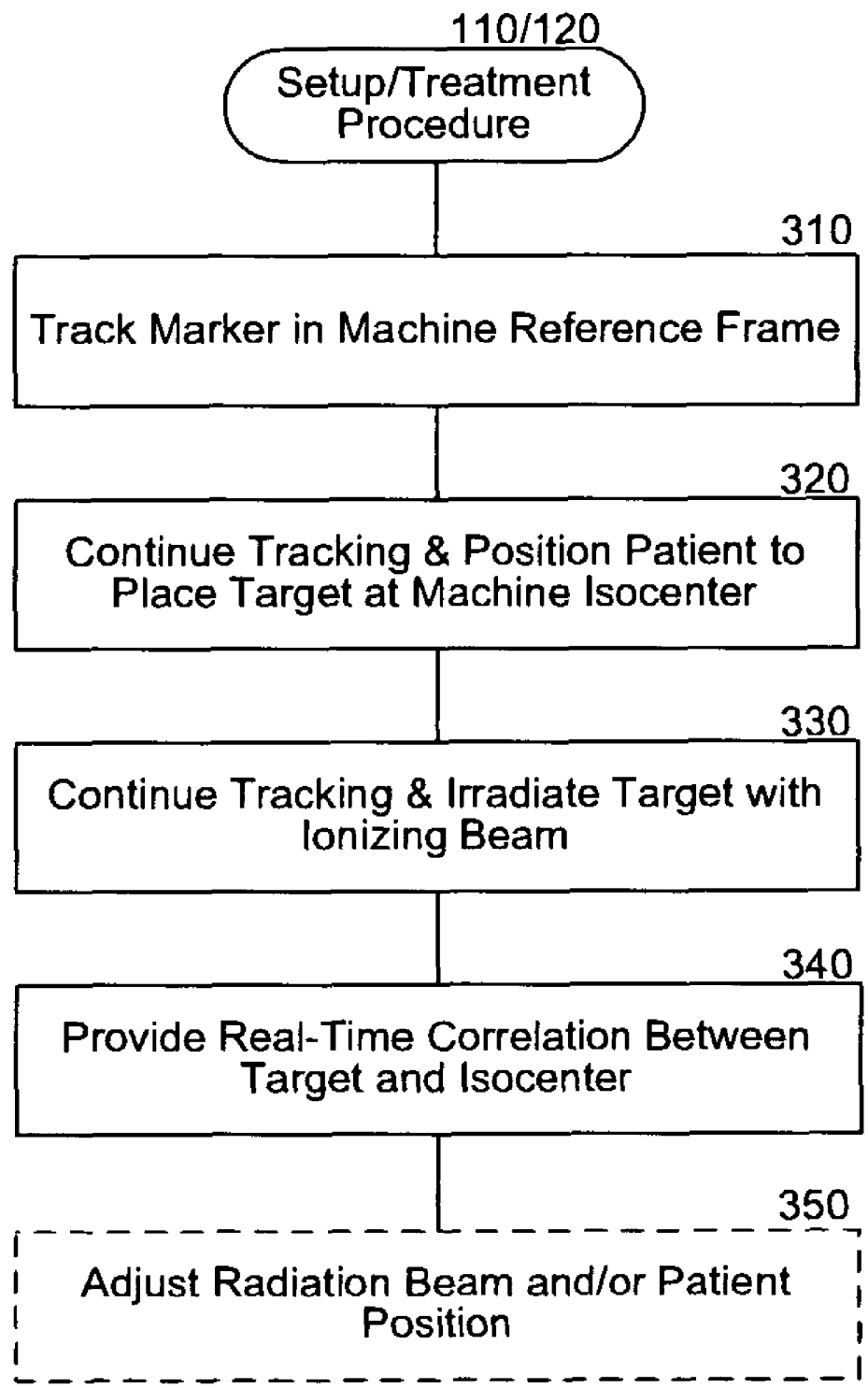
FIG. 4 is a flow diagram of setup and treatment procedures for a radiation therapy process in accordance with an embodiment of the invention.

FIG. 4 is a flow diagram of specific embodiments of the setup and treatment procedures (FIG. 2, Blocks 110 and 120). In one embodiment, the setup procedure includes a status check to confirm that the target parameters are still within the specifications of the treatment plan before irradiating the patient. For example, when the patient arrives at the treatment facility to undergo a treatment procedure, the patient can be placed in the observation area 24 (FIG. 1) and the localizing unit 26 (FIG. 1) can track the locations of the markers before irradiating the patient during a treatment procedure. The target trajectory and the target configuration can accordingly be determined from the marker locations. This aspect of the setup procedure can be highly beneficial because the target parameters can be confirmed to ensure they match the treatment plan before irradiating the patient without having to do a CT scan.

The setup and treatment procedures include a second tracking feature 310 in which the localizing unit 32 (FIG. 1) tracks the markers in the external reference frame of the radiation delivery device 30 (FIG. 1). The second tracking feature typically commences after placing the patient on a support table under the gantry of the radiation delivery device 30 and continues to the end of the treatment procedure. The localizing unit 32 is preferably a magnetic localization system that tracks the markers in the machine reference frame using a non-ionizing energy to acquire objective target treatment data related to the position of the target and the parameters of the target.

The setup and treatment procedures further include a positioning stage 320 in which the target is positioned relative to the machine isocenter of the radiation delivery device 30. In the positioning stage 320, the localizing unit 32 determines the locations of the markers in the machine reference frame and calculates an offset between the actual position of the target and the desired position of the target relative to the machine isocenter. The localizing unit 32 then provides an indication of the offset to a technician or a computer to move the table according to the calculated offset. The tracking feature 310 continues throughout the positioning stage 320 to continually update the offset between the actual location of a target and the desired position of the target relative to the machine isocenter. As such, a technician or an automatic system continues to move the table according to the calculated offset until the target is placed within an acceptable range of the desired position relative to the machine isocenter. In one embodiment, an alarm can be activated if the actual position of the target deviates from the desired target position after placing the target at the desired location.

The objective target treatment data obtained by the localizing unit 32 during positioning stage 320 can further be used to confirm that the target configuration and the target trajectory are within the specifications of the treatment plan shortly before irradiating the target with an ionizing beam. This confirmation step can be in lieu of or in addition to the status check described above. The confirmation step may be quite useful because sudden changes in the target that would otherwise not be identified in conventional processes can be monitored before and during each treatment session. Moreover, patients can get nervous and alter their normal breathing or other functions, and the localizing unit 32 can identify when this occurs and provide biofeedback for in-situ training of the patient. In one embodiment, an abnormal trajectory of the target can be noted while the patient is on the support table under the gantry, and the patient can be monitored until the trajectory of the target is within the planned trajectory from the planning procedure 102. This is expected to significantly enhance the precision with which tumors and other types of targets are irradiated.

The tracking feature 310 and the positioning stage 320 are also expected to significantly enhance the efficiency of the setup procedure (FIG. 2, Block 110). For example, because the technician can remain in the radiation vault with the patient throughout the setup procedure, the technician does not waste time traveling between the radiation vault and a shielded area to obtain stereotactic X-rays required by conventional systems. Moreover, the tracking feature 310 provides real-time objective position information of the markers that can be sent to a control system that automatically moves the support table to position the target at the machine isocenter. The tracking feature 310 can significantly reduce the time it takes to perform the positioning stage 320 so that more patients can be treated in the radiation vault per day.

The setup and treatment procedures continue with an irradiation stage 330. As explained above, the tracking feature 310 generally continues so that the location of the target in the machine reference frame can also be determined throughout the irradiation stage 330. In many applications, the method includes a monitoring feature 340 that operates concurrently with the irradiation stage 330 to provide a real-time correlation between the actual location of the target and the machine isocenter. The monitoring feature 340, for example, correlates objective location coordinates of the target at sequential time intervals throughout the treatment procedure with the radiation beam of the radiation delivery device 30.

The correlation between the target location and the machine isocenter from the monitoring feature 340 can be used to perform a dynamic adjustment feature 350 that adjusts a parameter of the radiation beam and/or the patient position in real time during the radiation stage 330. For example, the radiation beam can be terminated when the target moves out of a desired range and activated when the target is within the desired range (i.e., gated therapy). In another embodiment, the table supporting the patient can be moved automatically according to a calculated offset during the radiation stage 330 to maintain the target within a desired range of the machine isocenter. Both of these embodiments are particularly advantageous for treating lung and prostate cancers because they compensate for target movement caused by respiration or other body functions during the radiation stage 330. The objective target data from the localizing unit 32 can accordingly be integrated with the radiation delivery device 30 to provide dynamic adjustments to the radiation beam and/or the patient position while irradiating the patient to mitigate damage to healthy tissue adjacent the target.

F. Specific Embodiments of Treatment Management and Verification Procedures

Figure 5:
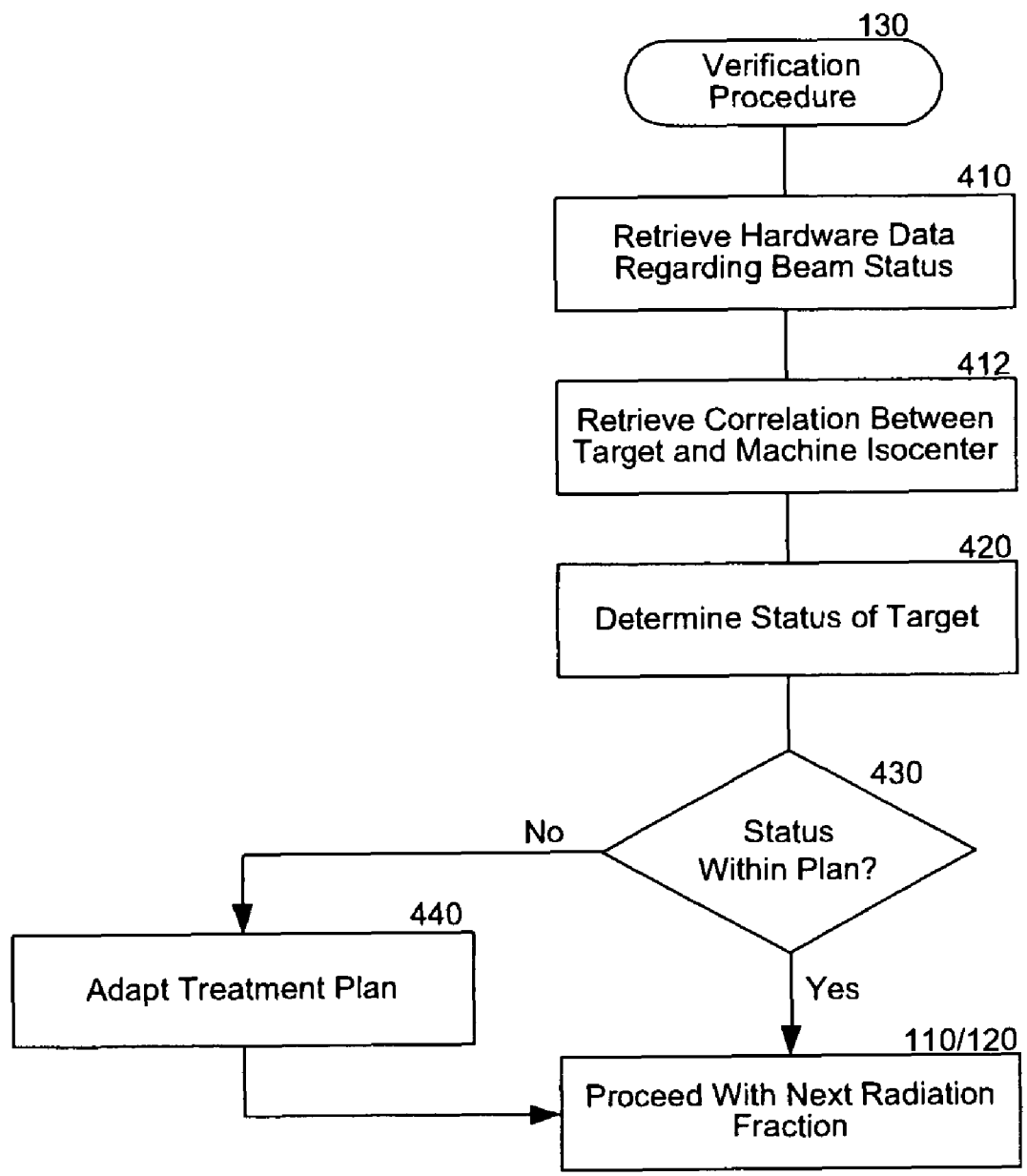
FIG. 5 is a flow diagram of record/verification and adaptive treatment planning procedures for a radiation therapy process in accordance with an embodiment of the invention.

FIG. 5 is a flow diagram illustrating a specific embodiment of the verification procedure (FIG. 2, Block 130). The verification procedure can include retrieving hardware data regarding the beam status (Block 410) and retrieving objective target data from one of the localizing units. For example, the verification procedure can include retrieving (a) the hardware data and (b) objective target data regarding the correlation between the actual location of the target and the machine isocenter (Block 412). The verification procedure further includes determining the status of the target (Block 420). In one embodiment, the status of the target is determined by correlating the hardware data with the actual location of the target at sequential time intervals of the irradiation procedure 330 (FIG. 4). The hardware data can include the beam intensity, beam position, collimator configuration, table position, accessory positions, and/or data related to any other aspect of equipment in the radiation vault at the sequential time intervals. The target status can be the cumulative radiation received at discrete areas of the target over one or more radiation fractions of the integrated process 100. The target status can also be the target configuration and/or the target trajectory throughout the setup procedure and the treatment procedure. The verification procedure 16 can occur on-line while irradiating the patient and/or off-line after completing a radiation fraction.

The verification procedure continues by assessing whether the status of the target is progressing according with the treatment plan (Block 430). If the target status is as planned, the procedure continues by repeating the setup procedure and the radiation procedure at the next planned radiation fraction. However, if the target status is not as planned, then the integrated process continues with an adaptive planning stage 440 in which the treatment plan is revised to adapt to the change in target status. After revising the treatment plan in the adaptive planning stage 440, the process continues with the setup procedure and the treatment procedure for the next radiation fraction according to the revised treatment plan.

Figure 6:
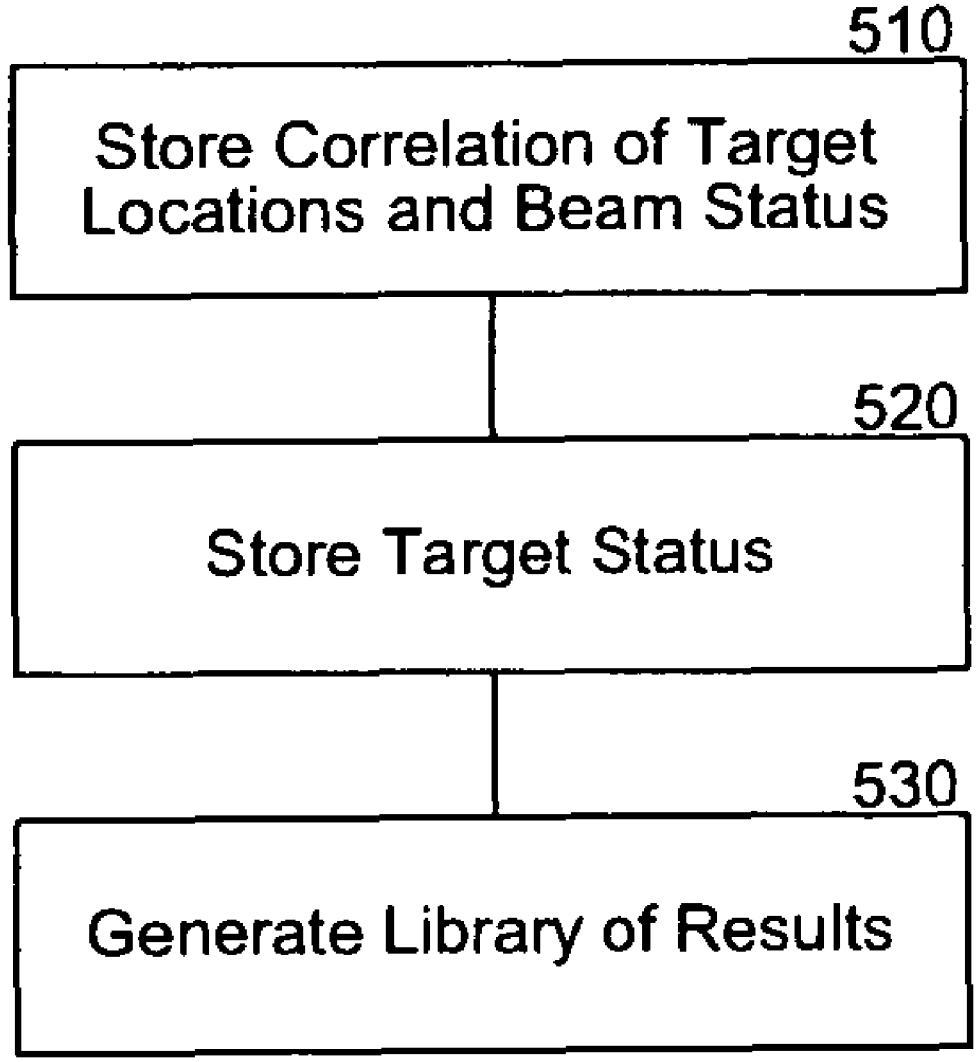
FIG. 6 is a flow diagram of a procedure for cataloging results of radiation fractions and treatment plans for a radiation therapy process in accordance with an embodiment of the invention.

FIG. 6 is a further aspect of the integrated process that includes storing the correlations of the actual target locations and the beam status in a memory (Block 510) and storing the target status in memory (Block 520). This aspect of the method includes generating a library of results over a number of patients that can be easily searched by practitioners to provide better estimates of the outcomes of specific treatment plans. A further aspect of this embodiment is to review the library for adjusting the treatment plans based on the observed characteristics of previous patients and/or previous radiation fractions of the same patient.

In general, the terms used in the following claims should not be construed to limit the invention to the specific embodiments disclosed in the specification, but rather the invention should be construed to include all integrated radiation therapy methods and systems that operate in accordance with the claims and any equivalents thereof. Accordingly, the invention is not limited, except as by the appended claims.

We claim:

1. A method of establishing a system for radiation therapy, comprising:

providing a first node having a first localization unit located in a first area of a facility, wherein the first localization unit is configured to autonomously locate a marker positioned within the patient with respect to a first external reference frame external to the patient;

providing a second node having a second localization unit located in a radiation vault containing a radiation delivery device, wherein the second localization unit is configured to autonomously locate the marker positioned within the patient with respect to a second external reference frame of the radiation delivery device; wherein the radiation therapy includes continuous treatment having multiple fractions and operatively coupling the first node to the second node by a network to transfer target data between the first and second nodes.

2. The method of claim 1 wherein the first and second localizing units locate the marker using a non-ionizing energy.

3. The method of claim 2 wherein the non-ionizing energy is magnetic energy.

4. The method of claim 1, further comprising providing a third node coupled to the network, wherein the third node comprises a verification module having a computer operable medium containing instructions that cause a computer to evaluate radiation delivered to the patient based at least in part on data from the second node.

5. The method of claim 1, further comprising providing a central information system coupled to the network for managing data from the first and second nodes.

6. A method of integrated radiation therapy, comprising:

acquiring objective planning data related to a parameter of a target within a patient in a first external reference frame external to the patient by periodically locating a marker positioned within the patient using a portable localization system at a treatment planning area;

moving the portable localization system to a radiation vault containing a radiation delivery device separate from the treatment planning area; and determining locations of the marker with respect to second external reference frame related to a machine isocenter of the radiation delivery device by periodically locating the marker in the radiation vault using the portable localizing system; wherein the radiation therapy includes continuous treatment having multiple fractions.

7. The method of claim 6 wherein the portable localization system uses a non-ionizing energy for locating the marker.

8. The method of claim 7 wherein the non-ionizing energy comprises magnetic energy.

9. A system for radiation therapy, comprising:

a first node having a first localization unit located in a first area of a facility, wherein the first localization unit is configured to autonomously locate a marker positioned within the patient with respect to a first external reference frame external to the patient;

a second node having a second localization unit located in a radiation vault containing a radiation delivery device, wherein the second localization unit is configured to autonomously locate the marker positioned within the patient with respect to a second external reference frame of the radiation delivery device; wherein the radiation therapy includes continuous treatment having multiple fractions and a network operatively coupling the first node to the second node to transfer target data between the first and second nodes.

10. The system of claim 9 wherein the first and second localizing units locate the marker using a non-ionizing energy.

11. The system of claim 10 wherein the non-ionizing energy is magnetic energy.

12. The system of claim 10, further comprising a third node coupled to the network, wherein the third node comprises a verification module having a computer operable medium containing instructions that cause a computer to evaluate radiation delivered to the patient based at least in part on data from the second node.

13. The system of claim 10, further comprising a central information system coupled to the network for managing data from the first and second nodes.

* * * * *